US00PP27517P2

(12) United States Plant Patent
Delabroye

(10) Patent No.: US PP27,517 P2
(45) Date of Patent: Dec. 27, 2016

(54) ***HEUCHERA* PLANT NAMED 'PICASSO'**

(50) Latin Name: ***Heuchera* hybrid**
Varietal Denomination: Picasso

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 100 days.

(21) Appl. No.: 14/121,867

(22) Filed: Oct. 28, 2014

(51) Int. Cl.
*A01H 5/02* (2006.01)

(52) U.S. Cl.
USPC ..... Plt./440

(58) Field of Classification Search
USPC ..... Plt./440
See application file for complete search history.

(56) References Cited

PUBLICATIONS

Retrieved from the Internet on Mar. 31, 2016—www.bloembollenvisie.nl/Nieuws/Paginas/HeucheraserieMasterPainters (1 pg total).*
Retrieved from the Internet on Apr. 4, 2016—www.freewebstore.org/heucheraholics/Heuchera_Picasso_Master_Painter/p3666016_15623475.aspx (5 pgs total).*
Retrieved from the Internet on Apr. 4, 2016—www.pepiniere-roche-saint-louis.fr/HEUCHERA-Picasso-cbaaaaUba.asp (3 pgs total).*
Retrieved from the Internet on Apr. 4, 2016—www.longfield-gardens.com/plantname/Heuchera-Picasso (2 pgs total).*

* cited by examiner

*Primary Examiner* — Susan McCormick Ewoldt
(74) *Attorney, Agent, or Firm* — Penny J. Aguirre

(57) ABSTRACT

A new cultivar of hybrid *Heuchera* named 'Picasso', that is characterized by its compact and mounded plant habit, its leaves with greyed-orange centers, yellow-green to yellow margins, and yellow-green veins, and its small pink flowers on dark red flowering stems.

2 Drawing Sheets

Botanical classification: *Heuchera* hybrid.
Cultivar designation: 'Picasso'.

BACKGROUND OF THE INVENTION

The present invention relates to a new and distinct cultivar of *Heuchera* of hybrid origin, botanically known as a *Heuchera* and is hereinafter referred to by its cultivar name 'Picasso'.

The new cultivar was discovered as a chance seedling in a trial field by the Inventor in Hantay, France in April of 2011. The trial field contained hundreds of cultivars and proprietary seedlings of *Heuchera* from the Inventor's breeding program. The exact parentage of 'Picasso' is therefore unknown.

Asexual propagation of the new cultivar was first accomplished under the direction of the Inventor by in vitro propagation in Rijswijk, The Netherlands in June of 2011. Asexual propagation of the new cultivar by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Picasso' as a new and unique cultivar of *Heuchera*.

1. 'Picasso' exhibits a compact and mounded plant habit.
2. 'Picasso' exhibits leaves with greyed-orange centers, yellow-green to yellow margins, and yellow-green veins.

3. 'Picasso' exhibits small pink flowers on dark red flowering stems.

'Picasso' can be most closely compared to the *Heuchera* cultivars 'Circus' (U.S. Plant Pat. No. 25,495) and 'Tiramisu' (U.S. Plant Pat. No. 20,429). Both are similar to 'Picasso' in their foliage coloration. 'Circus' differs from 'Picasso' in having a less compact plant habit, in having leaves that are larger in size, in having flowers that are larger in size and darker pink in color. 'Tiramisu' differs from 'Picasso' in having a less compact plant habit, in having less contrasting colors between the leaf blade and veins, and in having flowers that are white in color.

BRIEF DESCRIPTION OF THE DRAWINGS

The accompanying colored photographs illustrate the overall appearance and distinct characteristics of the new *Heuchera*. The photographs were taken of a plant three-years in age as grown in a garden bed in a poly covered unheated greenhouse in Hillegom, The Netherlands. The plant was placed in a container for the photograph.

The photograph in FIG. 1 provides a side view of the plant habit of 'Picasso' in bloom.

Figure 1:
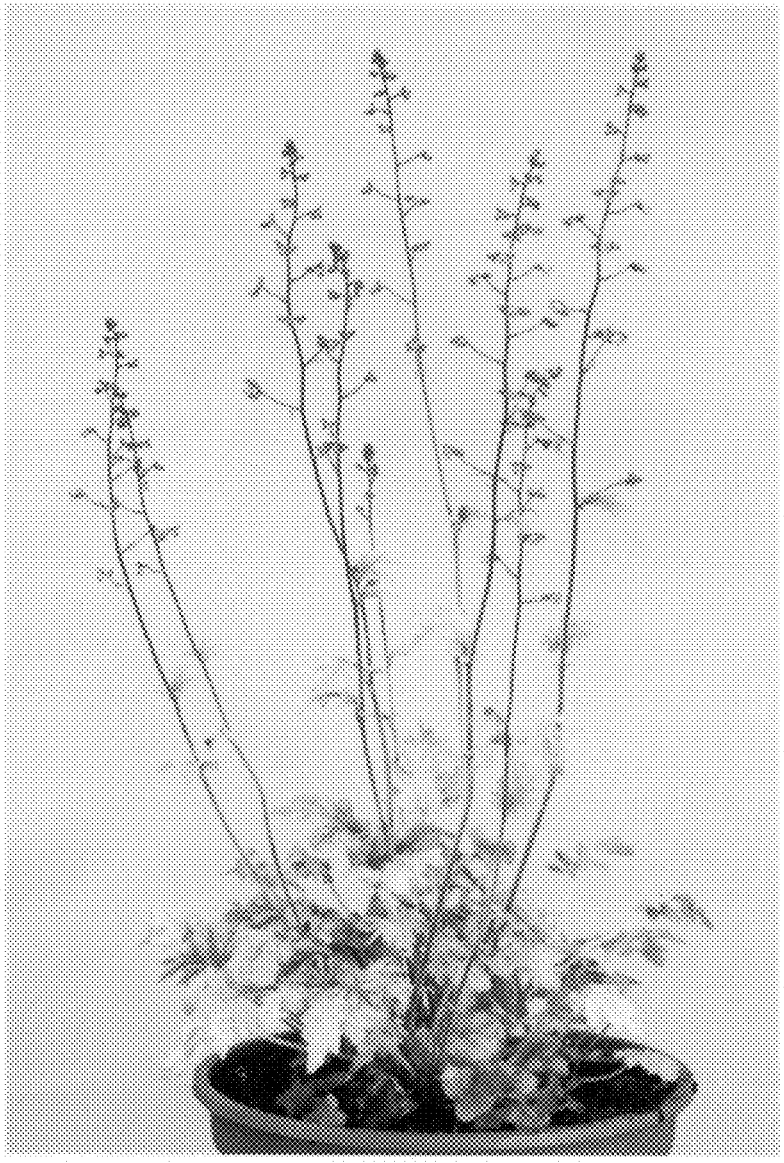
Figure 2:
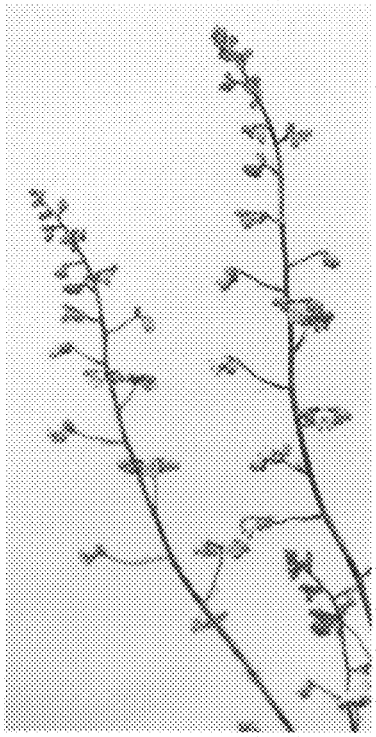

The photograph in FIG. 2 provides a close-up view of the inflorescences of 'Picasso'.

Figure 3:
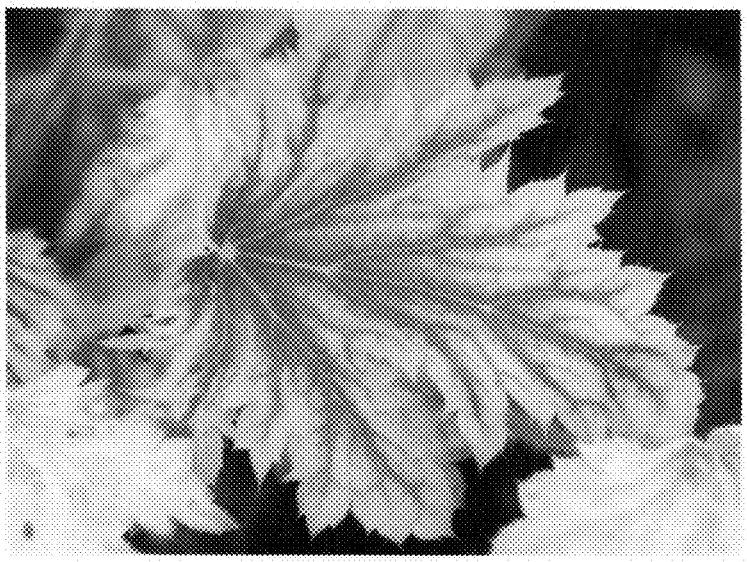

The photograph in FIG. 3 provides a close-up view of a leaf of 'Picasso'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of three year-old plants of 'Picasso' as grown in a garden bed in a poly covered unheated greenhouse in Hillegom, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—An average of 4 weeks from late spring into early summer in The Netherlands.

*Plant type*.—Herbaceous perennial.

*Plant habit*.—Compact and mounded foliage, clump-forming.

*Height and spread*.—An average of 60 cm in height (including inflorescences) and 40 cm in width in three years in a garden bed.

*Hardiness*.—At least in U.S.D.A. Zones 3 to 9.

*Diseases and pests*.—No particular susceptibility or resistance to pests and diseases has been observed.

*Root description*.—Fibrous roots on woody rootstalks.

*Propagation*.—In vitro propagation.

*Growth rate*.—Moderate.

Stem description (peduncle, flowering stem):

*Shape*.—Round.

*Stem color*.—A blend between 180A to 181A with base N170C.

*Stem size*.—Primary; an average of 3 mm in diameter and 56.8 cm in length (19 cm from base to apex of Inflorescence, secondary; an average of 0.75 mm in diameter and 1.9 cm in length.

*Stem strength*.—Moderate.

*Stem aspect*.—Average angle of primary peduncle; 80° (horizontal=0°), average angle of secondary peduncles; 70° to primary peduncle (=0°).

*Stem surface*.—Densely covered with soft, very short hairs an average of 2 mm in length and NN155C to NN155D in color.

*Stem number*.—Average of 12 flowering stems.

*Branching habit*.—Flowering stems emerge from basal rosette.

Foliage description:

*Leaf shape*.—Broad ovate.

*Leaf division*.—Simple.

*Leaf base*.—Ilastate, lobes free to touching.

*Leaf apex*.—Mucronate.

*Leaf venation*.—Laciniate, color; upper surface 153D and lower surface 150C to 150D, main veins on upper surface sparsely covered with soft short hairs; 0.5 mm in length and NN155C to NN155D in color, main and secondary veins on lower surface moderately covered with soft short hairs 0.5 mm in length and NN155C to NN155D in color.

*Leaf margins*.—Lobed with average of 7 lobes per leaf, lobe margins crenate with apices mucronate, moderately covered with short hairs 0.5 mm in length and NN155C to NN155D in color.

*Leaf attachment*.—Petiolate.

*Leaf arrangement*.—Alternate in basal rosettes.

*Leaf orientation*.—Typically nearly horizontal to slightly upward to petiole and slightly cupped downward.

*Leaf surface*.—Upper and lower surface; dull.

*Leaf color*.—In the spring and early summer young leaves upper surface; 176A irregularly margined with 151D and lower surface; 180D irregularly margined with 150B to 150C, in the summer and fall mature leaves upper surface; 175C to 175D irregularly margined with a blend of 153D and 11A, mature leaves lower surface; 174D irregularly margined with 11A, some leaves turn almost completely red (175D) in late summer and fall.

*Leaf size*.—An average of 6.1 cut in length and 5.8 cm in width.

*Leaf quantity*.—An average of 15 per basal rosette.

*Petioles*.—An average of 10.5 cm in length and 2 mm in diameter, color; N144A with base 174B to 174C, surface; densely covered with soft, very short hairs an average of 2 mm in length and NN155C to NN155D in color.

*Stipules*.—Small leafy stipules at the base of each leaf, narrow acute apex, an average of 1.2 cm in length and 3.5 mm in width, color; 150D with tips 145B.

Flower description:

*Inflorescence type*.—Numerous small bell-shaped flowers arranged as a compound spike on peduncles emerging from the base of the rosette.

*Inflorescence size*.—An average of 19.4 cm in height (excluding peduncle) and 5.3 cm in width.

*Inflorescence number*.—An average of 12 per 23-cm container.

*Flower fragrance*.—None.

*Flower quantity*.—Average of 120 flowers per flowering stem.

*Flower lastingness*.—Average of one week.

*Flower buds*.—Obovate in shape, an average of 4.5 mm in diameter and 2 mm in diameter, 47B with base 47D in color.

*Flower aspect*.—Outward to slightly drooping.

*Flower type*.—Single, campanulate.

*Flower size*.—An average of 6 mm in length and 5 mm in diameter.

*Petals*.—About 5, rotate arrangement and implanted in the hypanthium at base, narrow elliptic to narrow ovate and oblanceolate in shape, margin is entire, narrowly acute apex, upper and lower surface is dull and glabrous, color of upper and lower surface when opening; 65C and when fully open; 65C to 65D, an average of 3.5 mm in length and 1 mm in width.

*Calyx*.—Campanulate, sepals fused to hypanthium, 6 mm in length and 5 mm in diameter.

*Sepals*.—An average of 5, fused into campanulate hypanthium, elliptic in shape, an average of 6 mm in length and 2.5 mm in width, margin is entire and fused into hypanthium, acute apex, fused base, color; immature upper and lower surface; 47B with base 47D, mature upper and lower surface; 51D suffused with 148A towards the tip, upper and lower surfaces are dull and densely covered with very short glandular hairs an average of 0.1 mm in length and matched to the sepals in color.

*Pedicels*.—An average of 2 mm in length and 0.5 mm in diameter, 180A in color, moderate strength, average angle of main flower pedicel 0° (0°=horizontal), average angle of secondary flower pedicels 65° to main pedicel.

Reproductive organs:

*Gynoecium*.—An average of 2 pistils, 2 mm in length, stigma; pointed in shape, 155D in color, style; an average of 1.75 mm in length and 157A in color, ovary; 154A to 154B in color.

*Androcoecium*.—An average of 5 stamens, anthers; ovate in shape, about 0.5 mm in length and N170A in color, filament; 1 mm in length and 155A in color, pollen; low in quantity and 156D in color.

*Seed/fruit*.—No fruit or seeds were observed.

It is claimed:

1. A new and distinct cultivar of hybrid *Heuchera* plant named 'Picasso' as herein illustrated and described.

* * * * *